United States Patent [19]
Djokic et al.

[11] Patent Number: 5,498,699
[45] Date of Patent: Mar. 12, 1996

[54] COMPLEXES AND CHELATES OF AZITHROMYCIN WITH BIVALENT AND/OR TRIVALENT METALS AND THEIR USE AS ANTIULCER

[75] Inventors: Slobodan Djokic; Zlatko Vajtner; Hrvoje Krnjevic; Nevenka Lopotar; Lidija Kolacny-Babic, all of Zagreb, Yugoslavia

[73] Assignee: PLIVA Farmaceutska kemijska, prehrambena i kozmeticka industrija s.p.o., Croatia

[21] Appl. No.: 22,398

[22] Filed: Mar. 6, 1991

[30] Foreign Application Priority Data

Mar. 7, 1990 [YU] Yugoslavia ................... 455/90

[51] Int. Cl.$^6$ ............... C07F 5/00; A01N 43/04
[52] U.S. Cl. ............... 534/15; 514/29; 514/925
[58] Field of Search ............... 424/1.11, 1.24; 514/29, 925; 534/15

[56] References Cited

U.S. PATENT DOCUMENTS

| | | | |
|---|---|---|---|
| 3,622,627 | 11/1971 | Blackwood et al. | 552/205 |
| 3,862,225 | 1/1975 | Conover et al. | 552/205 |
| 3,937,694 | 2/1976 | Bathory et al. | 530/32 X |
| 4,886,792 | 12/1989 | Djokic et al. | 514/183 |
| 4,902,790 | 2/1990 | Mangia et al. | 536/13.7 |
| 4,963,528 | 10/1990 | Vajtner et al. | 514/29 |
| 4,997,959 | 3/1991 | Khanna et al. | 552/206 |
| 5,196,205 | 3/1993 | Borody | 424/653 |
| 5,246,708 | 9/1993 | von Borstel et al. | 424/650 |
| 5,348,946 | 9/1994 | Attardo et al. | 514/34 |

*Primary Examiner*—Gary Geist
*Assistant Examiner*—C. Harris
*Attorney, Agent, or Firm*—Pollock, Vande Sande & Priddy

[57] ABSTRACT

The invention relates to the use of complexes and chelates resp., of antibiotics with bivalent and/or trivalent metals in antiulcer drugs, to new complexes and chelates resp., of antibiotics with bivalent and/or trivalent metals and to processes for the obtaining thereof.

23 Claims, No Drawings

COMPLEXES AND CHELATES OF AZITHROMYCIN WITH BIVALENT AND/OR TRIVALENT METALS AND THEIR USE AS ANTIULCER

The present invention relates to the use of complexes and chelates resp., of antibiotics with bivalent and/or trivalent metals in the obtaining of antiulcer drugs, to new complexes and chelates resp., of antibiotics with bivalent and/or trivalent metals and to processes for the obtaining thereof.

It has been known that some organic compounds form metal complexes and chelates, thereby changing their physical-chemical properties (solubility, stability, melting point etc.) and the pharmacokinetics as well as the pharmacodynamics in biologically active compounds.

There was described (BE patent 892,357) the formation of $Co^{+2}$ complexes of macrolide antibiotics, especially of erythromycin, the starting substance for obtaining N-methyl-11-aza-10deoxo-10-dihydroerythromycin A (non-proprietary name azithromycin; proprietary name Sumamed® (PLIVA, Zagreb, Yugoslavia), whereas J. Pharm. Pharmac. 18, (1966) 727 asserts that with other divalent metal ions ($Cu^{+2}$, $Ca^{+2}$, $Mg^{+2}$, $Ni^{+2}$ and $Zn^{+2}$) no complexes are formed. On the contrary, we have found that azithromycin forms complexes with bivalent metals yielding products of a high antibiotic activity (HU patent 198,507)

It has been known that inter alia Al-Mg gel is applied as antacid in the treatment of duodenal or gastric ulcer giving relief to the gastric mucosa and keeping the pH of the gastric juice between 4.5 and 5.5. For the same purpose also some antibiotics have been used in order to eradicate the microorganisms *Helicobacter pylori* and *Campylobacter jejuni* which are allegedly one of the factors causing the development and the relapse of duodenal or gastric ulcers. Since it has been presumed that *Helicobacter pylori* inhabits the mucous region of the gastric membrane—whereby the often unsuccessful eradication and the resulting reoccurences have been explained—there have been applied ever increasing doses and durations of treatment with various antibiotics. Even azithromycin is no exception.

It has been found, and this represents one object of the present invention, that complexes and chelates resp., of antibiotics with bivalent and/or trivalent metals in the form of gels may be used in the obtaining of antiulcer drugs, which has not been as yet described according to the Applicants' Prior Art search.

Complexes and chelates resp., of antibiotics with bivalent and/or trivalent metals are novel and they represent a further object of the present invention.

A further object of the present invention are processes for the obtaining of complexes and chelates resp., of antibiotics with bivalent and/or trivalent metals in high yields as well as of pharmaceutical preparations indicated for the treatment of ulcer diseases.

Particularly there should be cited azithromycin.

As complex-and chelate-forming metals there are used metals of the II and III group, which form physiologically tolerated compounds.

Particularly there should be cited $Mg^{+2}$, $Al^{+3}$, $Fe^{+3}$, $Rh^{+3}$, $La^{+3}$, and $Bi^{+3}$.

The process for obtaining complexes and chelates resp., of azithromycin is performed by means of reacting the antibiotic in the form of free bases or salts, especially hydrochlorides, with salts of bivalent and/or trivalent metals such as $Mg^{+2}$, $Al^{+3}$, $Fe^{+3}$, $Rh^{+3}$, $La^{+3}$, and $Bi^{+3}$, especially chlorides, in a ratio of 2:1, at room temperature, in aqueous solution or in a mixture of water/alcohol, at a pH of 8.0–11.0, or with metal hydroxides and/or carbonates, subsalicylates or their gels, which are used as antacids such as aluminum hydroxide-magnesium carbonate, sucralfate and bismuth subsalicylate, in a ratio of 1:1 to 1:4. The process is most suitably performed with the antibiotic base in alcohol such as methanol or ethanol. The product is isolated in a conventional manner, e.g. By evaporation of the solvent (alcohol) from the reaction mixture under reduced pressure and the isolation of the product by means of filtration.

The product is formulated by known methods into pharmaceuticals such as granules or chewing tablets or aqueous suspensions.

It has been found that the azithromycin chelates with aluminum and magnesium in a ratio of 1:1 to 1:4, in the form of gels as well as with other gels, which are applied as antacids, are retained within 24 hours in the mucous region of the rat stomach in a 1.5- to 60-fold concentrations (Tables 1 and 2), which exceed the Minimal Inhibitory and Bactericidal Concentrations for *Helicobacter pylori* and *Campylobacter jejuni*; accordingly, said preparations are move indicated for the treatment of gastric diseases such as gastric or duodenal ulcers than the parent azithromycin. Further on, it has been demonstrated by toxicological investigations that the pharmaceutical formulations do not change the toxicity of the active ingredient.

TABLE 1

Concentration of azithromycin in the rat gastric mucosa upon one administration of 60 mg/rat p.o. of
azithromycin Al—Mg gel 1:1
azithromycin sucralfate gel 1:1
azithromycin bi-subsalicylate gel 1:1
in comparison with azithromycin (30 mg/rat p.o.)

| Time h | Azithromycin Al—Mg gel µg/g of tissue | Azithromycin sucralfate µg/g of tissue | Azithromycin bi-sub-salicylate µg/g of tissue | Azithromycin µg/g of tissue |
|---|---|---|---|---|
| 5 | $\bar{X} =$ 159.4 ± 28.66 | $\bar{X} =$ 100.2 ± 32.94 | $\bar{X} =$ 32.5 ± 8.60 | $\bar{X} =$ 99.4 ± 16.61 |
| 18 | $\bar{X} =$ 107.4 ± 32.04 | $\bar{X} =$ 75.1 ± 21.54 | $\bar{X} =$ 31.3 ± 10.02 | $\bar{X} =$ 98.3 ± 30.71 |
| 24 | $\bar{X} =$ 71.8 ± 20.41 | $\bar{X} =$ 74.5 ± 33.45 | $\bar{X} =$ 26.1 ± 5.26 | $\bar{X} =$ 1.3 ± 0.08 |
| 32 | $\bar{X} =$ 7.9 ± 2.88 | $\bar{X} =$ 36.6 ± 7.53 | $\bar{X} =$ 21.1 ± 3.90 | $\bar{X} = 0$ |

TABLE 2

Concentration of azithromycin in the rat duodenal mucosa upon one administration of 60 mg/rat p.o. of
azithromycin Al-Mg gel 1:1
azithromycin sucralfate gel 1:1
azithromycin bi-subsalicylate gel 1:1
in comparison with azithromycin (30 mg/rat p.o.)

| Time h | Azithromycin Al—Mg gel µg/g of tissue | Azithromycin sucralfate µg/g of tissue | Azithromycin bi-sub-salicylate µg/g of tissue | Azithromycin µg/g of tissue |
|---|---|---|---|---|
| 5 | $\bar{X} =$ 90.0 ± 14.78 | $\bar{X} =$ 98.1 ± 14.17 | $\bar{X} =$ 73.8 ± 20.77 | $\bar{X} =$ 103.5 ± 7.35 |
| 18 | $\bar{X} =$ 91.3 ± 13.46 | $\bar{X} =$ 82.8 ± 27.11 | $\bar{X} =$ 62.2 ± 20.55 | $\bar{X} =$ 86.1 ± 33.45 |
| 24 | $\bar{X} =$ 74.3 ± 29.00 | $\bar{X} =$ 55.8 ± 17.04 | $\bar{X} =$ 40.5 ± 13.33 | $\bar{X} = 0$ |
| 32 | $\bar{X} =$ 7.6 ± 1.07 | $\bar{X} =$ 35.6 ± 18.87 | $\bar{X} =$ 42.4 ± 11.25 | $\bar{X} = 0$ |

The invention is illustrated by the following Examples:

EXAMPLE 1

In 50 mL (0.02 mole) of a solution of azithromycin in 95% ethanol there were dissolved 0.067 g $AlCl_3$ (0.01M solution with respect to $Al^{+3}$) and upon adjusting the pH value to 8.6 with 0.1N NaOH it was kept stirring for 1 hour at room temperature in a nitrogen stream. Upon addition of 30 mL water the reaction mixture was evaporated under reduced pressure to about half its volume, whereupon it was kept stirring for two hours and the pH was kept constant (pH state) at 8.9 with 0.1N NaOH. The white precipitate was aspirated, washed with 3×10 mL of water and dried, yielding 0.68 g of the product (89.0%), m.p. 125°–128° C.

Analysis: Al(atomic absorption spectrometry method):
Calc.: 1.77%
Found: 1.73%
Activity: 852 E/mg *Sarcina lutea* ATCC 9341

EXAMPLE 2

In accordance with the process described in Example 1 with the sole exception that $AlCl_3$ was replaced by the addition of 0.136 g $FeCl_3 \times 6\ H_2O$ and the pH was kept at 9.0, there was obtained 0.72 g of a light grey product (92.5%); m.p. 130°–133° C.

Analysis: Fe(atomic absorption spectrometry method):
Calc.: 3.59%
Found: 3.71%
Activity: 840 E/mg *Sarcina lutea* ATCC 9341

EXAMPLE 3

0.750g of azithromycin were charged into a 100 mL flask and dissolved in 50 mL of water under the addition of 1N HCl (pH approx. 6.0). Subsequently, there were added 0.136 $FeCl_3 \times 6\ H_2O$ and it was kept stirring upon gradually adjusting the pH value to 8.9 with 0.1N NaOH. The reaction mixture was kept stirring for 2 hours at a constant pH value whereupon the light grey product was aspirated, washed with 3×10 mL of water, and dried. There was obtained 0.70 g of the product (89.9%). The analysis of the product was identical as in Example 2.

EXAMPLE 4

In accordance with the process described in Example 1 with the sole exception that $AlCl_3$ was replaced by the addition of 0.132 g $RhCl_3 \times 3\ H_2O$ there was obtained 0.67 g of a light grey product (83.6%); m.p. 120°–123° C.

Analysis: Rh(polarographic method; 1M pyridine - 1M KCl,
$E_{1/2}=-0.40$ V; SCE (Saturated Calomel Electrode)
Calc.: 6.42%
Found: 6.15%
Activity: 834 E/mg *Sarcina lutea* ATCC 9341

EXAMPLE 5

In accordance with the process described in Example 1 with the sole exception that $AlCl_3$ was replaced by the addition of 0.186 g of $LaCl_3 \times 7\ H_2O$ and the pH was kept at 9.2, there was obtained 0.66 g of a white product (80.5%); m.p. 118°–122° C.

Analysis: La(atomic absorption spectrometry method):
Calc.: 8.47%
Found: 8.10%
Activity: 830 E/mg *Sarcina lutea* ATCC 9341

EXAMPLE 6

In accordance with the process described in Example 1 with the sole exception that $AlCl_3$ was replaced by the addition of 0.158 g of $BiCl_3$, there was obtained 0.70 g of a product (82.0%).

Analysis: Bi(atomic absorption spectrometry method):
Calc.: 12.25%
Found: 12.00%
Activity: 812 E/mg *Sarcina lutea* ATCC 9341

EXAMPLE 7

In accordance with the process described in Example 3 with the sole exception that $FeCl_3$ was replaced by the addition of 0.102 g $MgCl_2 \times 6\ H_2O$ and the pH was kept at 8.6, there was obtained 0.55 g (75.0%) of a white product.

Analysis: Mg(atomic absorption spectrometry method):
Calc.: 1.22%
Found: 1.54%
Activity: 850 E/mg *Sarcina lutea* ATCC 9341

EXAMPLE 8

5.0 g of azithromycin were charged into a 100 mL flask and dissolved in 50 mL of methanol. Upon the addition of 5.0 g of aluminum hydroxide-magnesium carbonate gel it was kept stirring for 2 hours in a nitrogen stream. The suspension was then evaporated to dryness under reduced pressure and the obtained product (9.5 g) was air-dried.

Activity: 430 E/mg *Sarcina lutea* ATCC 9341

EXAMPLE 9

In accordance with the process described in Example 8 with the sole exception that 5.0 g of aluminum hydroxide-magnesium carbonate gel were replaced by 10.0 g thereof and that there were used 100 mL of 95% ethanol instead of methanol, there were obtained 14.3 g of the product.

Activity: 295 E/mg *Sarcina lutea* ATCC 9341

EXAMPLE 10

In accordance with the process described in Example 8 with the sole exception that 5.0 g of aluminum hydroxide-magnesium carbonate gel were replaced by 20.0 g thereof, there were obtained 23.5 g of the product.

Activity: 160 E/mg *Sarcina lutea* ATCC 9341

EXAMPLE 11

In accordance with the process described in Example 8 with the sole exception that aluminum hydroxide-magnesium carbonate gel was replaced by 5.0 g of sucralfate, there were obtained 9.5 g of the product.

Activity: 435 E/mg *Sarcina lutea* ATCC 9341

EXAMPLE 12

In accordance with the process described in Example 8 with the sole exception that aluminum hydroxide-magnesium carbonate gel was replaced by 5.0 g of bismuth subsalicylate, there were obtained 9.3 g of the product.

Activity: 420 E/mg *Sarcina lutea* ATCC 9341

We claim:
1. A method for treating a patient suffering from ulcers which comprises administering to said patient a pharmaceu- tical preparation containing an amount effective for treating ulcers of a complex or chelate of an azithromycin with bivalent or trivalent metals or both.

2. The method as claimed in claim 1, wherein the metals are chosen from $Mg^{+2}$, $Al_{+3}$, $Fe^{+3}$, $Rh^{+3}$, $La^{+3}$, and $Bi^{+3}$.

3. The method as claimed in claim 1, containing chelates of azithromycin with antacids chosen from the group of salts of Al, Mg, and Bi, which is in the form of a gel.

4. The method as claimed in claim 2, containing chelates of azithromycin with aluminum hydroxide-magnesium carbonate, which is in the form of a gel.

5. The method as claimed in claim 2, containing chelates of azithromycin with sucralfate which is in the form of a gel.

6. The method as claimed in claim 2, containing chelates of azithromycin with bismuth-subsalicylate, which is in the form of a gel.

7. Chelate of azithromycin with bivalent or trivalent metals or both.

8. A chelate of claim 7 with aluminum hydroxide-magnesium carbonate in the form of gels.

9. A chelate of claim 7 with sucralfate in the form of gels.

10. A chelate of claim 7 with bismuth-subsalicylate in the form of gels.

11. Complex or chelate of azithromycin with $Mg^{+2}$ or trivalent metal or both.

12. Complex and chelate as claimed in claim 11, wherein the metals are chosen from $Mg^{+2}$, $Al_{+3}$, $Fe^{+3}$, $Fe^{+3}$, $Rh^{+3}$, $La^{+3}$, and $Bi^{+3}$.

13. Complexes and chelates of claim 11 with antacids selected from the group consisting of salts of Al, Mg, and Bi in the form of gels.

14. The complexes and chelates of claim 11 wherein the metal is $Mg^{+3}$.

15. The complexes and chelates of claim 11 wherein the metal is $Al^{+3}$.

16. The complexes and chelates of claim 11 wherein the metal is $Fe^{+3}$.

17. The complexes and chelates of claim 11 wherein the metal is $Rh^{+3}$.

18. The complexes and chelates of claim 11 wherein the metal is $La^{+3}$.

19. The complexes and chelates of claim 11 wherein the metal is $Bi^{+3}$.

20. The complexes and chelates of claim 12 wherein the ratio of azithromycin to said metal is 1:1 to 1:4.

21. The complexes and chelates of claim 20 wherein said ration is 1:2.

22. The process for preparing a chelate of an azithromycin with complex metal salt wherein said slat is selected from the group consisting of aluminum hydroxide-magnesium carbonate, bismuth subsalicylate, and bismuth sucralfate which comprises reacting said azithromycin with said salt in an alcohol, in a weight ratio of 1:1 to 1:4, and evaporating said alcohol to obtain a dry residue to thereby isolated said chelate.

23. The process of claim 22 wherein said alcohol is methanol or ethanol.

* * * * *